(12) United States Patent
Itoh

(10) Patent No.: US 6,997,874 B2
(45) Date of Patent: Feb. 14, 2006

(54) NONCONTACT OPHTHALMOTONOMETER

(75) Inventor: Hiroshi Itoh, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 166 days.

(21) Appl. No.: 10/280,001

(22) Filed: Oct. 25, 2002

(65) Prior Publication Data
US 2003/0097053 A1    May 22, 2003

(30) Foreign Application Priority Data
Nov. 19, 2001  (JP)  ............................. 2001-353555

(51) Int. Cl.
A61B 3/16  (2006.01)

(52) U.S. Cl. ........................................ 600/401

(58) Field of Classification Search ............... 600/401, 600/558, 405, 561, 399; 351/221, 205, 208
See application file for complete search history.

(56) References Cited

U.S. PATENT DOCUMENTS

| | | | | |
|---|---|---|---|---|
| 4,665,923 A | * | 5/1987 | Kobayashi | ............... 600/401 |
| 4,995,393 A | * | 2/1991 | Katsuragi et al. | ........... 600/401 |
| 5,532,769 A | | 7/1996 | Miwa et al. | |
| 5,764,341 A | * | 6/1998 | Fujieda et al. | ............... 351/221 |
| 5,807,273 A | * | 9/1998 | Suzuki | ....................... 600/558 |
| 5,894,337 A | | 4/1999 | Okinishi et al. | |
| 5,989,195 A | * | 11/1999 | Iijima et al. | ................ 600/561 |
| 6,193,372 B1 | | 2/2001 | Okumura et al. | |

FOREIGN PATENT DOCUMENTS

| | | |
|---|---|---|
| JP | 8-10225 | 1/1996 |
| JP | 2001-275985 | 10/2001 |

* cited by examiner

*Primary Examiner*—Max F. Hindenburg
*Assistant Examiner*—Brian Szmal
(74) *Attorney, Agent, or Firm*—Fitzpatrick, Cella, Harper & Scinto

(57) ABSTRACT

In a noncontact ophthalmotonometer: an image processing operation is performed on an image signal subjected to an imaging operation to extract a pupil, to compute location of the center of gravity thereof, and to move a measuring mechanism so that the center of gravity is located at the central axis of a nozzle. Locations of two alignment mark images from the signal are detected to compute distance from a nozzle end to a cornea from a gap between centers of gravity of the mark images. When the nozzle end approaches the cornea, the mechanism moves away therefrom. The mechanism moves toward an eye in the direction of the nozzle central to detect a second mark image. An aligning operation is performed using the second mark image. Eye pressure is then measured. The mechanism moves to a location farthest from the eye in the direction of the nozzle central axis.

5 Claims, 6 Drawing Sheets

NONCONTACT OPHTHALMOTONOMETER

BACKGROUND OF THE INVENTION

1. Field of the Invention

The present invention relates to a noncontact ophthalmotonometer used to measure pressure of an eye to be examined at an ophthalmic hospital or the like.

2. Description of the Related Art

Hitherto, in a noncontact ophthalmotonometer, pressure required to deform a cornea by a predetermined amount is determined by blowing fluid onto an eye to be examined in order to measure pressure of the eye to be examined from the determined required pressure.

In such a noncontact ophthalmotonometer, in order to achieve precise measurement, a gap between a nozzle, mounted to the central portion of an optical member, and the vertex of the cornea of the eye to be examined needs to be precisely provided.

Conventionally, a method of aligning a noncontact ophthalmotonometer with respect to an eye to be examined by operation of a joystick or upper and lower rings by an examiner and a method of aligning a noncontact ophthalmotonometer in which, as disclosed in Japanese Patent Laid-Open No. 8-10225, the noncontact ophthalmotonometer automatically precisely aligns itself with an eye to be examined after an examiner has performed an aligning operation by a certain amount have been proposed.

In a noncontact ophthalmotonometer, since the distance between the nozzle and the vertex of a cornea is short, a stopper is provided as a safety device to prevent the nozzle from coming closer to an eye to be examined than a certain distance, so that the nozzle does not come into contact with the eye to be examined. After a subject has placed his chin onto a chin support, the examiner moves the noncontact ophthalmotonometer towards the eye to be examined while looking through it from beside it. When the examiner judges that the noncontact ophthalmotonometer has reached a limit as to how close it can be moved towards the eye to be examined, the stopper operates.

However, in the conventional method in which an examiner performs an aligning operation, a considerable amount of time is required to complete measurements depending on how skilled the examiner is, thereby placing a burden on the subject.

Even if a noncontact ophthalmotonometer is made capable of aligning itself to an optimal position after an examiner has aligned it to a position near the optimal position, it is still necessary for the examiner to align the noncontact ophthalmotonometer to a position near the optimal position. Thus, the level of skill required to align the noncontact ophthalmotonometer has not been adequately lowered.

As regards the safety device, even if the stopper is set prior to carrying out measurements, when a subject moves his head after the stopper has been set, it is necessary to reset the stopper, so that the measurements become more troublesome and time-wasting.

SUMMARY OF THE INVENTION

It is an object of the present invention to overcome the above-described problems and to provide a noncontact ophthalmotonometer which allows an examiner to easily and safely measure a fundus to be examined regardless of the level of skill of the examiner.

To this end, according to the present invention, there is provided a noncontact ophthalmotonometer comprising a first alignment mark for detecting a rough distance between the cornea of an eye to be examined and an end of a nozzle and rough horizontal/vertical positional displacements thereof; a second alignment mark, which is provided inside an ophthalmotonometrical optical system and which is projected onto the eye to be examined through the nozzle, for detecting a more accurate distance and more accurate horizontal/vertical positional displacements than those detected using the first alignment mark; and imaging means for performing an imaging operation on an anterior eye part and the first and second alignment marks. In the noncontact ophthalmotonometer, by the first alignment mark that has been subjected to an imaging operation by the imaging means, a gap between the cornea and the nozzle is computed in order to set a movable range thereof in a direction of a central axis of the nozzle, and the ophthalmotonometrical optical system is moved in three-dimensional directions for alignment. In addition, the second alignment mark is detected in order to more precisely align the ophthalmotonometrical optical system in three-dimensional directions. When the alignment is completed, pressure of the eye is measured. When the measurement is completed, a housing is moved to a location which is situated farther away from the eye to be examined than the distance at which the eye to be examined is measured.

By controlling the noncontact ophthalmotonometer as described above, the pressure of the eye can be easily and safely measured.

According to another aspect of the present invention, a method of measuring eye pressure using a noncontact ophthalmotonometer comprises the steps of performing an aligning operation by controlling the driving means based on a relationship between a position of the first mark image and the center of a pupil of the eye to be examined that have been subjected to the imaging operation by the imaging means so that an optical axis of the ophthalmotonometrical optical system and the center of the pupil are in a predetermined relationship; determining a movable range of the ophthalmotonometrical optical system in a direction of a central axis of the nozzle by computing a gap between the eye to be examined and the nozzle from the first mark image; detecting the second mark image portions divided by the light-beam separating member by moving the ophthalmotonometrical optical system with respect to the eye to be examined within the determined movable range; performing another aligning operation which is more precise than the aligning operation based on the first mark image by controlling the driving means based on the second mark image portions; after completing the more precise aligning operation, measuring eye pressure; and after completing the measurement of eye pressure, moving the nozzle farther away from the eye to be examined than where the nozzle was at the time of the measurement of eye pressure.

Further objects, features and advantages of the present invention will become apparent from the following description of a preferred embodiment with reference to the attached drawings.

DESCRIPTION OF THE PREFERRED EMBODIMENT

A description of the present invention will be given in detail based on an illustrated embodiment.

Figure 1:
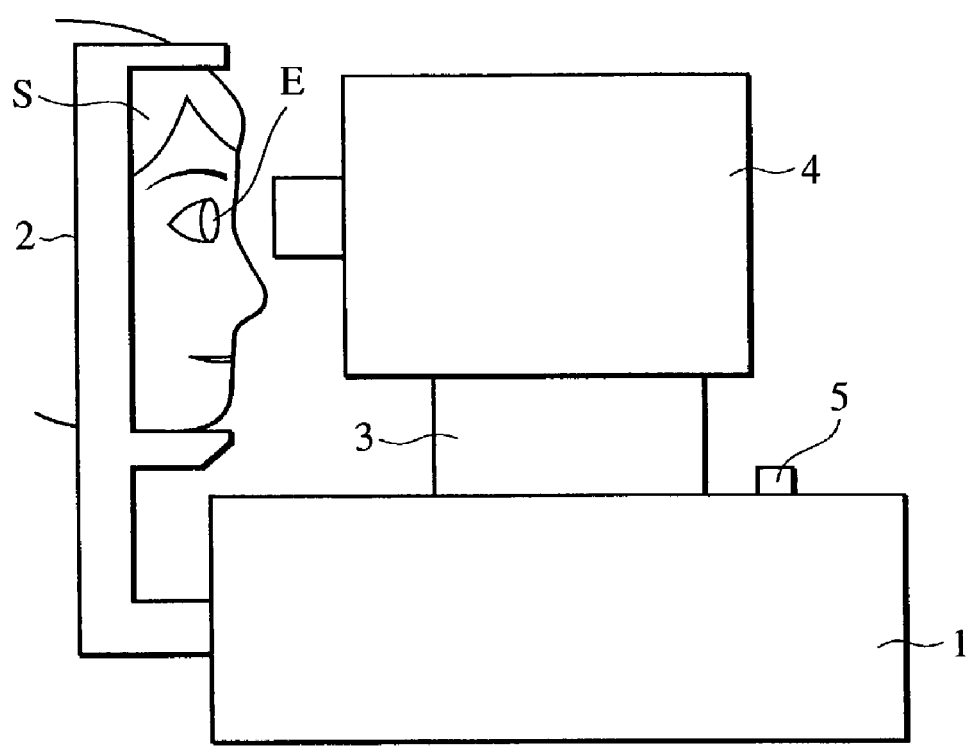
FIG. 1 is a schematic structural view of an embodiment of the present invention.

FIG. 1 is a schematic structural view of a noncontact ophthalmotonometer of an embodiment of the present invention. A chin support 2 for placing the head of a subject S is provided at a base 1. A housing 4 for accommodating an ophthalmotonometrical optical system is placed at the top surface of the base 1 through driving means 3, so that the driving means 3 can drive the housing 4 in three-dimensional directions. A measurement switch 5 for starting measurement is also provided on the base 1.

Figure 2:
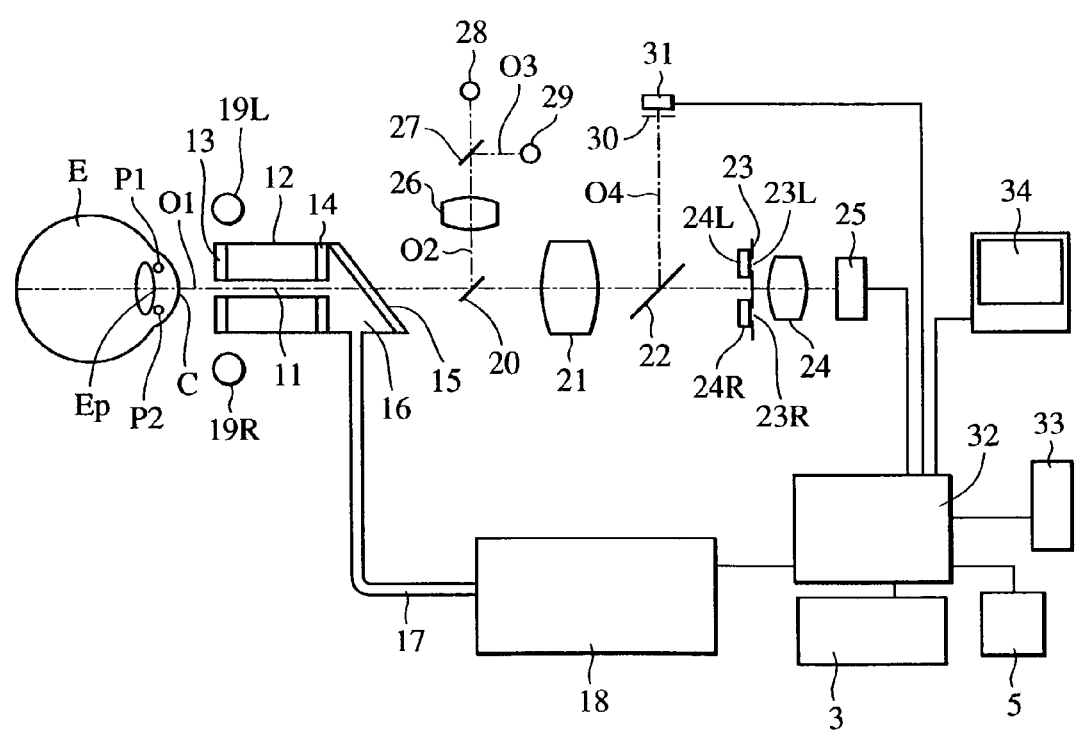
FIG. 2 is a structural view of an optical system as viewed from above the optical system.

FIG. 2 is a structural view of the ophthalmotonometrical optical system accommodated inside the housing 4 as viewed from above the ophthalmotonometrical optical system. A nozzle 11 is held by a cylindrical holding member 12 through transparent optical members 13 and 14, and a transparent window 15 is provided at the back portion of the holding member 12. A pressure chamber 16 is provided between the nozzle 11 and the window 15, and pressurizing means 18 is connected to the pressure chamber 16 through a tube 17. A pair of first alignment mark light sources 19L and 19R having a wavelength of, for example, 780 nm are disposed at symmetrical locations with respect to a light path O1, obliquely from an eye E to be examined externally of the holding member 12. Like the exit of the nozzle 11, light-beam exiting surfaces of the light sources 19L and 19R are disposed at a distance of the order of 10 mm from the eye E to be examined so as to allow a wide range of a cornea C of the eye E to be illuminated.

The nozzle 11, the window 15, a small mirror 20, a lens 21, a light-dividing member 22, an aperture plate 23, a lens 24, and an area array sensor 25 are successively disposed in the light path O1 forwardly of the eye E to be examined. Two small holes 23L and 23R are provided in the aperture plate 23 at locations which are symmetrical with respect to the light path O1. Wedge-shaped prisms 24L and 24R are provided as light-beam separating means at the small holes 23L and 23R, respectively.

A lens 26, a light-dividing member 27, and a second alignment mark light source 28, which serves as an ophthalmotonometrical light source and which is an infrared emitting diode (IRED) having a wavelength of, for example, 880 nm, are disposed in a light path O2 provided in the direction in which light is incident upon the small mirror 20. A light source 29 for fixation is disposed in a light path O3 provided in the direction in which light is incident upon the light-dividing member 27. A slit 30 and a cornea deformation sensor 31 for measuring eye pressure are disposed in a light path O4 provided in the direction of reflection of light from the light-dividing member 22. A filter for passing only wavelength of light from the second alignment mark light source 28 is attached to the back surfaces of the wedge-shaped prisms 24L and 24R.

Outputs of the area array sensor 25 and the cornea deformation sensor 31 are connected to a control section 32. The pressurizing means 18, the driving means 3 (which is, for example, a stepping motor) for driving the housing 4, the measurement switch 5, computing means 33 for computing a gap between a pair of alignment mark images P1 and P2, and a monitor 34 for displaying an image that has been subjected to an imaging operation are connected to the control section 32.

In an aligning operation, a light beam from the second alignment mark light source 28 illuminates the eye E to be examined. A second mark image reflected by the cornea C of the eye E to be examined passes through the small holes 23L and 23R of the aperture plate 23, and is subjected to an imaging operation at the area array sensor 25. At this time, portions of the second mark image used for the aligning operation are focused on different locations of the area array sensor 25 by the wedge-shaped prisms 24L and 24R.

However, although the second mark image is suitable for a precise aligning operation, it can only be detected when it is near an optimal alignment location because a receiving light beam tends to be subjected to vignetting by the nozzle 11 when the central axis of the nozzle 11 and the eye E to be examined are considerably decentered in the horizontal or vertical direction.

In examining the eye, the housing 4 in which the ophthalmotonometrical optical system is mounted is made to wait at a location farthest from the eye E in the direction of the central axis of the nozzle 11. The subject S places his chin onto the chin support 2, and a light beam from the fixation light source 29 passes through the light paths O3, O2, and O1 and illuminates the eye E. The eye E views the fixation light source 29, disposed on a line extending from the light path O1, through the nozzle 11. By illuminating the anterior part of the eye E to be examined with the pair of first alignment mark light sources 19L and 19R, the first alignment mark images P1 and P2 are projected onto the cornea C. Light reflected from the cornea C impinges upon the area array sensor 25 through the optical members 13 and 14, the window 15, the lens 21, the light-dividing member 22, the aperture plate 23, and the lens 24.

Figure 3:
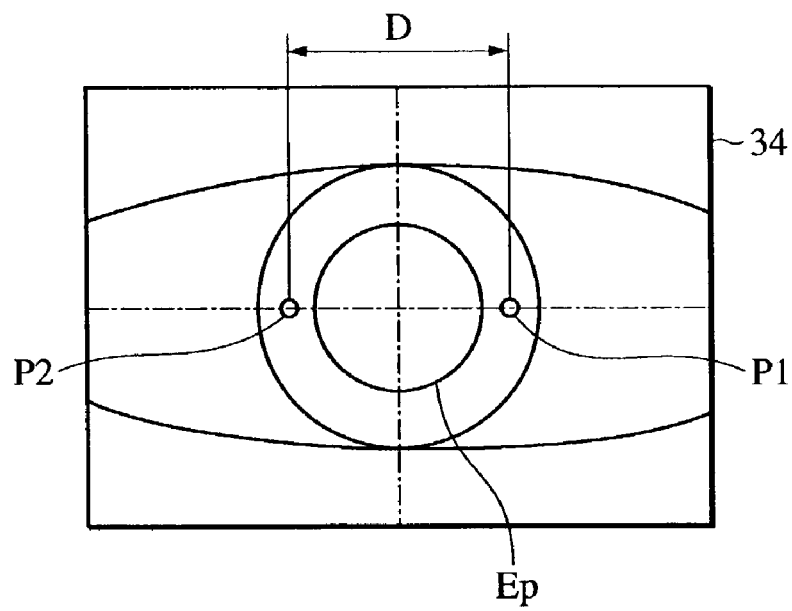
FIG. 3 illustrates a screen displaying an anterior part of an eye and first alignment mark images.

In the area array sensor 25, when the alignment mark images P1 and P2, the central axis of the nozzle 11, and the center of a pupil Ep are aligned, the two alignment mark images P1 and P2 are focused at locations on the monitor 34 that are symmetrical with respect to the central axis direction of the nozzle 11, as shown in FIG. 3. The point of intersection of the broken lines shown in FIG. 3 indicates the location of the central axis of the nozzle 11.

Figure 4:
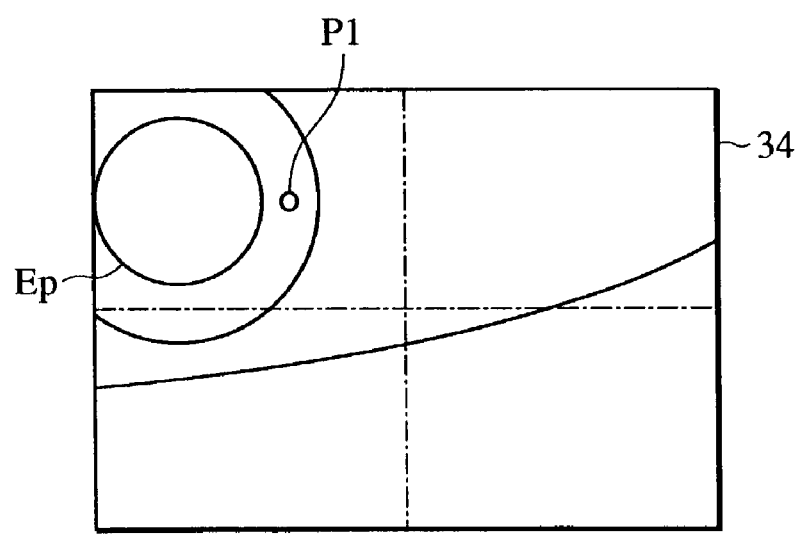
FIG. 4 illustrates the screen displaying the anterior part of the eye and one of the first alignment mark images.

However, when the central axis of the nozzle 11 and the pupil Ep of the eye E are out of alignment, the two alignment mark images P1 and P2 are displaced along with the pupil Ep, so that, as shown in FIG. 4, only the alignment mark image P1 may be subjected to an imaging operation.

Figure 5:
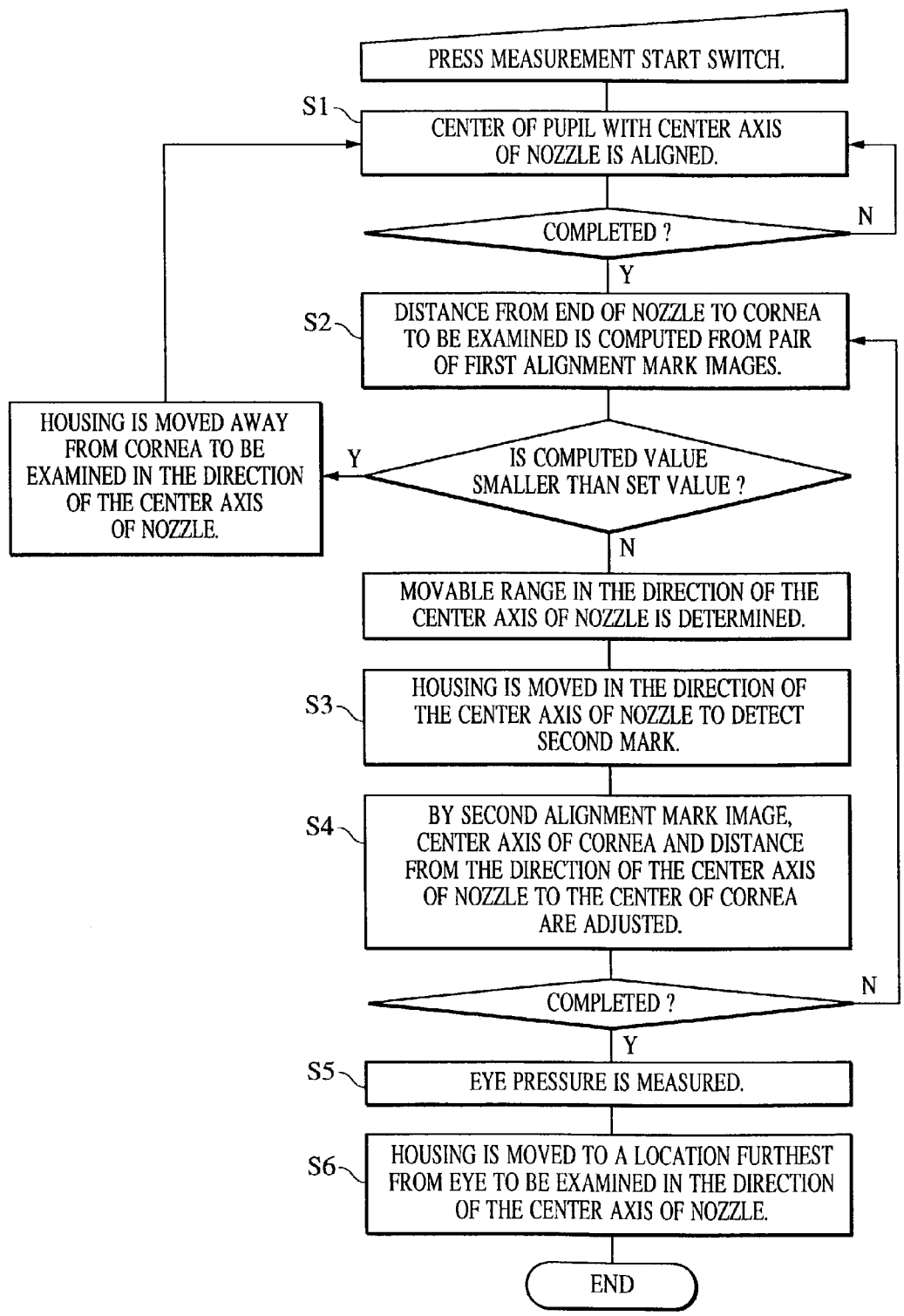
FIG. 5 is a flowchart which illustrates the steps carried out to measure pressure of the eye.

FIG. 5 shows a flowchart of the steps carried out from alignment to measurement eye pressure. First, the examiner views the pupil Ep of the eye E to be examined that appears on the monitor 34 as shown in FIG. 4. In other words, after confirming that it has been subjected to an imaging operation by the area array sensor 25, the examiner presses the measurement switch 5 to start carrying out measurements.

In Step S1, the control section 32 performs an image processing operation, such as a binary image processing operation, on an image signal that has been imaged by the area array sensor 25. From a set threshold value, the pupil Ep is extracted and the location of the center of gravity is computed. The housing 4 accommodating the ophthalmotonometrical optical system is moved by the driving means 3 so that the location of the center of gravity is situated at the location of the central axis of the nozzle 11 as shown in FIG. 3.

When Step S1 is completed, Step S2 is carried out. In Step S2, the control section 32 causes the computing means 33 to detect the positions of the pair of alignment mark images P1 and P2 from the image signal that has been provided by the area array sensor 25, to compute the positions of the centers of gravity of the corresponding alignment mark images P1 and P2, and to compute the distance from an end of the nozzle 11 to the cornea C based on a gap D between the positions of the centers of gravity (see FIG. 3). The control section 32 refers to a data table based on the result of calculation of the computing means 33 to determine how much the housing 4 can be moved in the direction of the central axis of the nozzle 11. This makes use of the fact that, when the nozzle 11 approaches the eye E to be examined, the gap D becomes large.

The minimum distance between the cornea C and an end of the nozzle 11 is previously set as a set value at the control section 32 so that the end of the nozzle 11 does not come into contact with the cornea C. When the result of calculation of the computing means 33 becomes less than the set value, that is, when the end of the nozzle 11 approaches the cornea C, the control section 32 causes the driving means 3 to be driven in order to move the housing 4 away from the cornea C in the direction of the central axis of the nozzle 11.

The gap D between the pair of alignment mark images P1 and P2 measured by the computing means 33 differs depending on the radius of curvature of the cornea C of the eye E. However, the distance which is determined by the control section 32 is a rough value, so that it does not have to be an exact value. Since the primary purpose of determining the distance is to prevent the end of the nozzle 11 from coming into contact with the cornea C, if the set value is provided taking into consideration that the positions of the alignment mark images P1 and P2 differ due to differences in the radius of curvature of the cornea C, it is possible to make full use of the safety function of preventing contact.

If the distance of movement of the housing 4 is set at a value of the order of a few mm, the housing 4 may be moved based on the calculation of the gap D in Step S2 instead of returning to Step S1. In addition, the housing 4 may be constructed so that it stops where it is instead of moving away from the cornea C.

Figure 6:
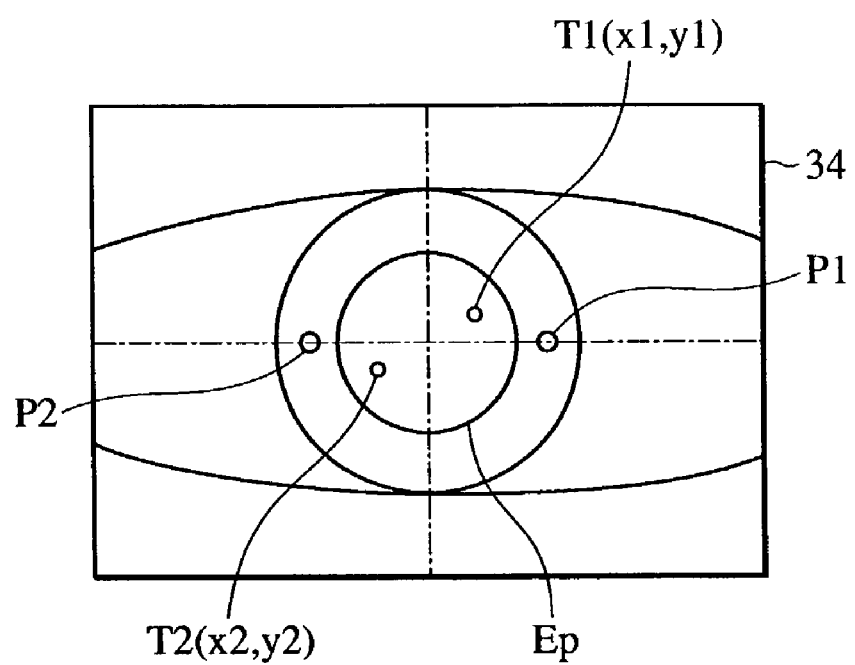
FIG. 6 illustrates the screen displaying the anterior part of the eye, the first alignment mark images, and second alignment mark image portions.

In Step S3, the control section 32 causes the driving section 3 to move the housing 4 accommodating the ophthalmotonometrical optical system towards the eye E to be examined in the direction of the central axis of the nozzle 11 in order to detect second mark image portions T1 and T2 of the second alignment mark light source 28 shown in FIG. 6.

In Step S4, using the second mark image portions T1 and T2 detected in Step S3, precise alignment is carried out. In FIG. 6, there is displacement in the direction of the central axis of the nozzle 11.

In aligning, the control section 32 computes coordinates T1 (x1, y1) and coordinates T2 (x2, y2) of the corresponding mark image portions T1 and T2, and center coordinates T (xt, yt).

FIG. 7 shows the center of the cornea C by an intersection point C (x0, y0) of an x coordinate axis and a y coordinate axis. When the central axis of the nozzle 11 and the center of the cornea C are vertically out of alignment, as shown in FIG. 7A, y1 and y2 are the same and x0 and xt are the same with respect to the center of the cornea C (x0, y0), but y0 and yt are different in the y direction. Therefore, the control section 32 performs a controlling operation so that the housing 4 is moved in the vertical direction by the driving means 3 in such a way that y0 and yt become the same.

Figure 7A:
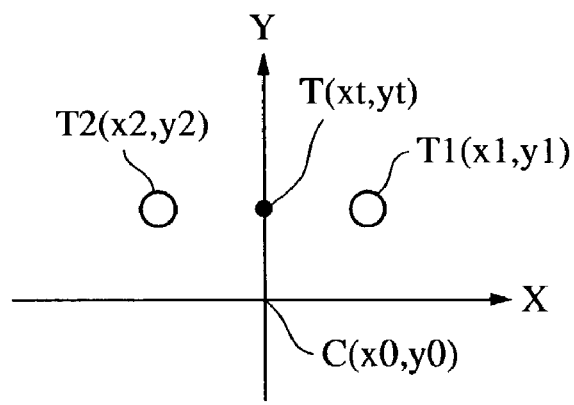
FIGS. 7A to 7D illustrate screens showing the second alignment mark image portions.
Figure 7B:
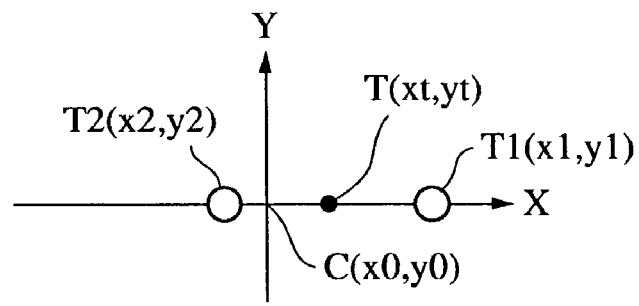

Similarly, when the central axis of the nozzle 11 and the center of the cornea C are horizontally out of alignment, as shown in FIG. 7B, y1 and y2 are the same, but x0 and xt are different. Therefore, the control section 32 performs a controlling operation so that the housing 4 is moved in the horizontal direction in such a way that x0 and xt become the same.

Figure 7C:
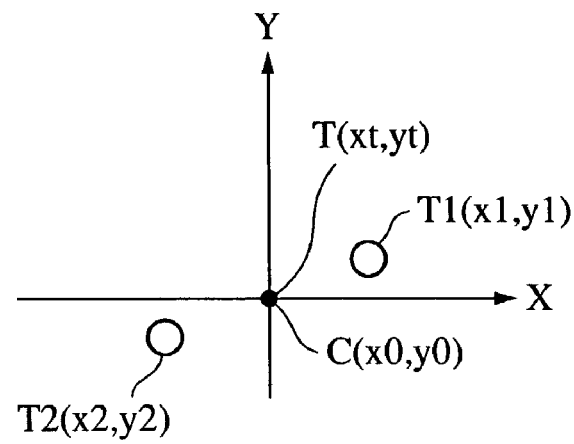

When the direction of the central axis of the nozzle 11 and the center of the cornea C are out of alignment in an operation distance direction, as shown in FIG. 7C, the position of the center of gravity coincides with the center of the cornea C, but x1 and x2 and y1 and y2 are different, respectively. Therefore, the control section 32 performs a controlling operation so that the housing 4 is moved in the direction of the central axis of the nozzle 11 in such a way that the coordinates y1 and y2 become the same.

Figure 7D:
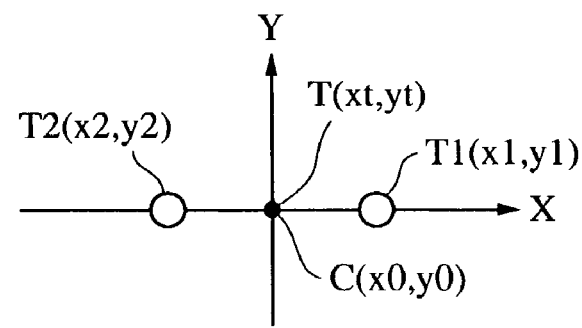

When the alignment is completed, as shown in FIG. 7D, the two mark image portions T1 and T2 are aligned on the x axis at equal distances from the center of the cornea C, so that the center coordinates T (xt, yt) and the coordinates of the cornea center C (x0, y0) are the same.

When the alignment is completed, Step S5 is carried out. In Step S5, the control section 32 outputs a signal to the pressurizing means 18 to measure eye pressure. Lastly, in Step S6, when the measurement of the eye pressure has been completed, the control section 32 causes the driving means 3 to move the housing 4 in the direction of the central axis of the nozzle 11 to a location which is situated farthest from the eye E.

By carrying out the above-described steps, one eye pressure measurement is completed. However, it is not necessary to carry out all of the steps; eye pressure may be measured by carrying out only some of the six Steps S1 to S6.

In the embodiment, the noncontact ophthalmotonometer is constructed so that, by carrying out Step S6, the housing 4 accommodating the ophthalmotonometrical optical system is moved in the direction of the central axis of the nozzle 11 to a location which is situated farthest from the eye E. However, the housing 4 may be moved to a location at a distance which is larger than the assumed operating distance, that is, the distance to an end of the nozzle 11 from the assumed position of the cornea C of the eye E.

Although, in the embodiment, a pair of first alignment mark light sources 19L and 19R are provided with respect to the central axis of the nozzle 11, other types of light sources, such as annular light sources, which are symmetrical at points with respect to the central axis of the nozzle 11 may be used.

The ophthalmotonometrical optical system is constructed so that it is moved to a location which is situated farthest from the eye E to be examined after measuring eye pressure, with this location being an initial location thereof prior to the measurement of eye pressure. However, it goes without saying that the ophthalmotonometrical optical system is at the same location after electrical power is applied to the noncontact ophthalmotonometer.

As described above, the noncontact ophthalmotonometer according to the present invention provides the following advantages. First, it makes it possible for the examiner to complete alignment and measurement by only pressing a measurement start switch, so that the examiner is not required to have so much skill in operating the noncontact ophthalmotonometer. Therefore, even if the examiner is not used to handling the noncontact ophthalmotonometer, unnecessary burden is not placed on the subject because the time required for measuring eye pressure is not long. In addition, since the movable range in the direction of the central axis of the nozzle is determined from the first alignment mark images, the nozzle is not brought too close to the eye to be examined. Further, by situating the initial position of the ophthalmotonometrical optical system farther away from the eye to be examined than the operating distance, it is possible to eliminate the possibility of the optical members or the nozzle coming into contact with the eye even if the head is moved.

Second, it is possible to minimize the possibility of the optical members, the nozzle, or the like coming into contact with the subject's face or eye to be examined when the subject places his head on the chin support. Since the ophthalmotonometrical optical system is at a location which is farthest from the eye to be examined in the direction of the central axis of the nozzle, the subject does not feel pressured when he places his head on the chin support.

Third, it is no longer necessary for the examiner to go to the trouble of, after the subject has placed his face onto the chin support prior to measuring eye pressure, bringing the noncontact ophthalmotonometer closer to the eye to be examined while viewing through it from beside it, and mechanically setting a stopper position when the examiner has judged that the noncontact ophthalmotonometer has reached a limit as to how close it can be moved towards the eye to be examined. In addition, although, conventionally, it has been necessary to reset the stopper every time the subject moves his head during alignment, it is not necessary to reset a stopper in the noncontact ophthalmotonometer of the present invention because the distance from an end of the nozzle to the eye to be examined is computed from the first alignment mark images. Even if the subject moves his head, so that the operating distance between the eye to be examined and the nozzle becomes smaller than the set value, the ophthalmotonometrical optical system is moved away from the eye to be examined, so that it is possible to eliminate the possibility of the ophthalmotonometrical optical system coming into contact with the eye.

Fourth, since a pair of first alignment mark light sources disposed symmetrically with respect to the central axis of the nozzle are provided, the computing means can easily perform computation. Since only two spots appear on the monitor when the examiner views an image that has been subjected to an imaging operation by the imaging means, the examiner can easily view the anterior part of the eye.

While the present invention has been described with reference to what is presently considered to be the preferred embodiment, it is to be understood that the invention is not limited to the disclosed embodiment. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A noncontact ophthalmotonometer comprising:
    an ophthalmotonometrical optical system, which equips a nozzle for discharging fluid toward a cornea of an eye to be examined in order to deform the cornea for measuring eye pressure based on deformation of the cornea;
    first detecting means for detecting a position of the nozzle with respect to the eye to be examined;
    second detecting means for detecting a position of the nozzle with respect to the eye to be examined,
        the second detecting means having a higher precision of position detection than that of the first detecting means,
        the second detecting means detecting the position of the nozzle with respect to the eye to be examined within a narrower range of the positions of the noncontact ophthalmotonometer than those within which the first detecting means detects the position of the nozzle with respect to the eye to be examined;
    driving means for driving the nozzle; and
    control means for controlling the first detecting means, the second detecting means, and the driving means,
    wherein the control means determines the position of the nozzle with respect to the eye to be examined in accordance with the detection by the first detecting means and determines a moving range of the nozzle toward the eye to be examined,
    wherein the control means controls the driving means so as to move the nozzle within the range of the positions of the noncontact ophthalmotonometer within which the second detecting means detects the position of the nozzle with respect to the eye to be examined, and
    wherein the control means controls the driving means after the movement of the nozzle within the range of the positions of the noncontact ophthalmotonometer within which the second detecting means detects the position of the nozzle with respect to the eye to be examined so as to move the nozzle toward a predetermined position based on the detected position detected by the second detecting means.

2. A noncontact ophthalmotonometer according to claim 1, wherein after finishing a pressure measurement, the control means controls the driving means so as to move the nozzle to the nozzle's farthest position from the eye to be examined.

3. A noncontact ophthalmotonometer according to claim 1, wherein the first detecting means comprises:
    an alignment mark light source for projecting a pair of alignment mark images on symmetrical positions with respect to a central axis of the nozzle;
    imaging means for performing an imaging operation on reflected images of the pair of alignment mark images, which are reflected at an anterior part of the eye to be examined, together with an image of the anterior part of the eye; and
    computing means for computing the position of the nozzle with respect to the eye to be examined based on positions of the anterior part of the eye and the pair of alignment mark images, which are subjected to the imaging operation.

4. A noncontact ophthalmotonometer according to claim 2, wherein the second detecting means comprises a second alignment mark light source for projecting a second alignment mark image through the nozzle, a light-beam separating means for dividing the second alignment mark image reflected on an anterior part of the eye to be examined, imaging means for performing an imaging operation on the divided second alignment mark image together with an image of the anterior part of the eye, and a computing means for computing the second position of the nozzle with respect to the eye to be examined based on positions of the anterior part of the eye and the divided second alignment mark image, which are subjected to the imaging operation.

5. A controlling method for controlling a noncontact ophthalmotonometer including an ophthalmotonometrical optical system, which equips a nozzle for discharging fluid toward a cornea of an eye to be examined in order to deform the cornea for measuring eye pressure based on deformation of the cornea, first detecting means for detecting a position of the nozzle with respect to the eye to be examined, and second detecting means for detecting a position of the nozzle with respect to the eye to be examined, the second detecting means having a higher precision of position detection than that of the first detecting means, the second detecting means detecting the position of the nozzle with respect to the eye to be examined within a narrower range of the positions of the noncontact ophthalmotonometer than those within which the first detecting means detects the position of the nozzle with respect to the eye to be examined, said method comprising the steps of:

detecting a position of the nozzle with respect to the eye to be examined by the first detecting means;

determining a moving range of the nozzle toward the eye to be examined;

moving the nozzle within the determined moving range and the range of detection of the second detecting means; and after the movement of the nozzle performed in said moving step, moving the nozzle to a predetermined position based on the detected position detected by the second detecting means.

* * * * *

UNITED STATES PATENT AND TRADEMARK OFFICE
CERTIFICATE OF CORRECTION

PATENT NO. : 6,997,874 B2 Page 1 of 1
APPLICATION NO. : 10/280001
DATED : February 14, 2006
INVENTOR(S) : Hiroshi Itoh It is certified that error appears in the above-identified patent and that said Letters Patent is hereby corrected as shown below:

ON THE TITLE PAGE
At Item (57), Abstract, line 12, "central" should read --central axis--.

COLUMN 4
Line 59, "measurement" should read --measurement of--.

Signed and Sealed this

Fifteenth Day of August, 2006

JON W. DUDAS
*Director of the United States Patent and Trademark Office*